United States Patent [19]

Nafissi-Varchei

[11] 4,348,406
[45] Sep. 7, 1982

[54] NOVEL GUANIDINE DERIVATIVES

[75] Inventor: M. Mehdi Nafissi-Varchei, North Caldwell, N.J.

[73] Assignee: Schering Corporation, Kenilworth, N.J.

[21] Appl. No.: 198,424

[22] Filed: Oct. 20, 1980

[51] Int. Cl.³ .................. A23L 3/34; C07C 79/46; C07C 149/40; C07C 143/67; A01N/47/10; A01N/43/84; A01N/43/48; A01N/43/40;

[52] U.S. Cl. .................. 424/300; 424/248.5; 424/248.52; 424/248.59; 424/248.55; 424/250; 424/263; 424/267; 424/283; 426/532; 260/112.5 R; 560/9; 560/12; 560/13; 560/16; 560/22; 560/29; 546/186; 546/193; 546/224; 546/244; 546/264; 546/348; 544/78; 544/111; 544/124; 544/130; 544/163; 544/164; 544/359; 544/360; 544/382; 549/424

[58] Field of Search .............. 544/78, 111, 124, 130, 544/163, 164, 359, 360, 382; 424/300, 248.5, 248.52, 248.54, 248.55, 250, 263, 267, 283; 426/532; 260/345.8 R, 112.5 R; 560/9, 12, 13, 16, 22, 29; 546/186, 193, 224, 244, 264, 348

[56] References Cited

U.S. PATENT DOCUMENTS 3,941,824  3/1976  Fuchs .................. 560/9
4,097,673  6/1978  Fuchs .................. 560/22

Primary Examiner—Alan Siegel
Attorney, Agent, or Firm—Anita W. Magnatti; Paul H. Ginsburg; Bruce M. Eisen

[57] ABSTRACT

Compounds of the formula:

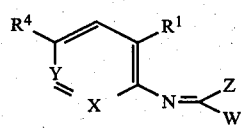

and their pharmaceutically acceptable acid addition salts, useful as anthelmintics are disclosed.

9 Claims, No Drawings

NOVEL GUANIDINE DERIVATIVES

The present invention relates to novel guanidine derivatives.

The compounds of the present invention are compounds of the formula:

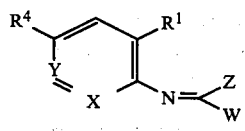

as well as the pharmaceutically acceptable acid addition salts thereof, wherein one of X and Y is $CR^5$ and the other is CH or N; one of Z and W is $-NR^3R^2$ and the other of Z and W is $-NHCO_2R^6$, wherein $R^6$ is selected from $C_1$ to $C_6$ alkyl and $C_1$ to $C_6$ alkyl substituted with $C_1$ to $C_6$ alkoxy, hydroxy or amino; $R^1$ is hydrogen, halo, nitro, or $-NHR^7$, wherein $R^7$ is

or $-SO_2R^8$, wherein $R^8$ is $C_1$ to $C_6$ alkyl, $C_1$ to $C_6$ alkyl substituted with phenyl or with halo, phenyl, or phenyl substituted with $C_1$ to $C_6$ alkyl or with halo; $R^2$ and $R^3$ are independently selected from hydrogen, N-alkyl piperidyl, wherein the alkyl group has 1 to 4 carbon atoms (e.g. N-methyl piperidyl), tetrahydropyranyl, morpholinyl, piperidyl, $C_1$ to $C_6$ alkyl and $C_1$ to $C_6$ alkyl substituted with hydroxy, $-SCH_3$, $-COOR^{10}$, piperazinyl, pyridyl, amino, substituted amino, $-COR^9$, wherein $R^9$ is $C_1$ to $C_6$ alkyl, $C_1$ to $C_6$ acyl, or a peptide residue having up to three amino acids, wherein the substituents on the substituted amino are selected from $C_1$ to $C_6$ alkyl,

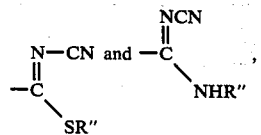

wherein $R^{10}$ is hydrogen or $C_1$ to $C_6$ alkyl and $R^{11}$ is $C_1$ to $C_6$ alkyl; $R^4$ and $R^5$ are independently selected from $C_1$ to $C_6$ alkyl, $C_1$ to $C_6$ alkoxy, $C_1$ to $C_6$ alkylthio, $C_1$ to $C_6$ alkylsulfoxide, phenoxy, phenylsulfonyl, phenylthio and phenylsulfoxy, with the proviso that at least one of $R^4$ and $R^5$ must be hydrogen, $C_1$ to $C_6$ alkyl or $C_1$ to $C_6$ alkoxy; and $R^6$ is selected from $C_1$ to $C_6$ alkyl, $C_1$ to $C_6$ alkyl substituted with $C_1$ to $C_6$ alkoxy, hydroxy or amino. In the aforementioned compounds, the alkyl groups may be linear, branched or cyclic and halo includes fluorine, chlorine, bromine and iodine.

Preferably, $R^1$ is nitro, $R^4$ is $C_1$ to $C_6$ alkylthio, $R^5$ is hydrogen, X and Y are CH, one of Z and W is $NHCO_2R^6$, wherein $R^6$ is $C_1$ to $C_6$ alkyl, and the other of Z and W is $NR^3R^2$, wherein $R^3$ is hydrogen and $R^2$ is $C_1$ to $C_6$ alkyl substituted with $-COOR^{10}$, pyridyl, amino or substituted amino, wherein the substituents on the substituted amino are selected from $C_1$ to $C_6$ alkyl and

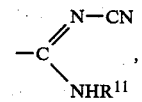

wherein $R^{10}$ is $C_1$ to $C_6$ alkyl and $R^{11}$ is $C_1$ to $C_6$ alkyl.

The present invention also relates to methods of preparing the aforementioned compounds and to the use of said compounds as anthelmintics.

The following reaction scheme illustrates the preparation of the compounds of the present invention

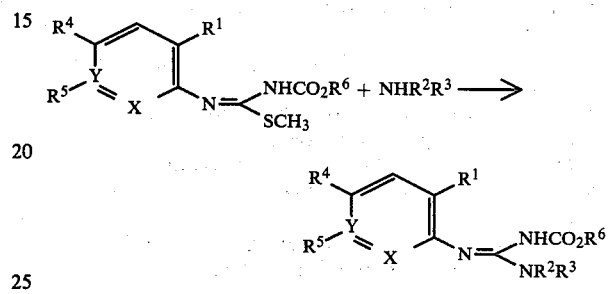

In the above scheme, $R^1$, $R^2$, $R^3$, $R^4$, $R^5$, $R^6$, Y and X are as defined above. This method is further illustrated by the Example.

The compounds of the present invention that are acid addition salts may be prepared by reacting the free base form of a compound of the present invention with an acid such as hydrochloric acid, hydrobromic acid, sulfuric acid, phosphoric acid, acetic acid, proprionic acid, succinic acid, pamoic acid, caproic acid, palmitic acid or stearic acid.

The following Example further illustrates the preparation of the compounds of the present invention:

EXAMPLE

N-Methoxycarbonyl-N'-[beta-ethyl-[N'-cyano-N''-methyl guanidino-N''-[2-nitro-4-propylthiophenyl]-guanidine Dissolve 6.7 g of N-Methoxycarbonyl-N'-[2-nitro-4-propylthiophenyl]-S-methyl-isothiourea and 3.7 g N-beta-aminoethyl-N'-cyano-N''-methyl-guainidine in 50 ml of acetonitrile by heating. Stir the resulting solution for 24 hours at ambient temperature. Remove the solvent by evaporation and chromatograph the residue on 350 g of silica gel, eluting with 1% methanol in methylene chloride to give the title product, melting at 72°–73° C.

Similarly, prepare the following compounds:
N-carbomethoxy-N'-(2-nitro-5-propyloxyphenyl)-N''-[beta-diethylaminoethyl)guanidine;
N-carbomethoxy-N'-[beta-(N'-cyano-N''-methyl-guanidinoethyl)]-N''-[2-nitro-5-propyloxyphenyl]-guanidine;
N-carbomethoxy-N'-[beta-diethyolaminoethyl)-N''-[2'-nitro-4'-propylthiophenyl]guanidine;
N-carbomethoxy-N'-[beta-(N'-cyano-N''-methyl-guanidinoethyl)]-N''-[2-nitro-4'-propylthiophenyl]-guanidine;
N-carbomethoxy-N'-[beta-diethylaminoethyl]-''-[2-nitro-5-phenylthiophenyl]guanidine;
N-carbomethoxy-N'-[beta-diethylaminoethyl]-N''-[2-nitro-5-propylthiophenyl]guanidine;

N-carbomethoxy-N'-[beta-(N'-cyano-N''-methyl-guanidinioethyl)]-N''-[2-nitro-5-propylthiophenyl]guanidine;

N-carbomethoxy-N'-[beta-(N'-cyano-N''-methyl-guanidinoethyl)]-N''-[2-nitro-5-phenylthiophenyl]guanidine;

N-carbomethoxy-N'-[beta-(N'-cyano-N''-methyl-guanidinoethyl)]-N''-[2-acetamido-4-methyl-5-propyloxyphenyl]guanidine;

N-carbomethoxy-N'-[2-pyridylmethyl]-N''-[2-nitro-4-propyloxyphenyl]guanidine;

N-carbomethoxy-N'-[2-nitro-5-propylthiophenyl]guanidine;

N-carbomethoxy-N'-[2-nitro-5-phenylthiophenyl]guanidine;

N-carbomethoxy-N'-[2-nitro-5-propyloxyphenyl]guanidine;

N-carbomethoxy-N'-[ethoxycarbonylmethyl]-N''-[2-nitro-5-propyloxyphenyl]guanidine;

N-carbomethoxy-N'-[4-propyloxyphenyl]guanidine;

N-carbomethoxy-N'-[2-chloro-4-propyloxyphenyl]guanidine;

N-carbomethoxy-N'-[beta-piperazinoethyl]-N''-[2-nitro-5-propylthiophenyl]guanidine.

The compounds of the present invention are useful in combatting helminths, i.e. in treating humans and animals suffering from an infestation of parasitic worms, for example, roundworms, hookworms, whipworms or tapeworms, by administering to the host animal a therapeutic amount of a compound of the present invention.

The compounds of this invention exhibit significant anthelmintic effects when administered to a host (e.g. swine, dogs or ruminants) at doses as low as about one milligram per kilogram of body weight per day in dosing over several days, or at about fifty milligrams per kilograms in a single day dosing, according to techniques well known in the art.

The optimum dose for each species of animal and for each type of parasite can readily be determined by one skilled in the art of using standard techniques such as the Modified McMaster Egg Counting Technique as described by H. B. Whitlock and H. McL. Gordon, J. Council Scientific Industrial Research (Australia) 12, p. 50, 1939 and H. B. Whitlock, J. Council Scientific Research (Australia) 21, p. 177, 1948.

From these, and similar tests, anthelmintic efficacy is assessed by determining the number of eggs in feces passed on the days following treatment with the compound compared with pretreatment days. In addition, autopsy of animals after treatment will indicate whether the infection has been eradicated. Based on experimentation, proper dosages for curing various infections can be determined.

The compounds of this invention may be administered in suspensions, capsules, feed additive preparations, tablets, etc. as is well known to those skilled in the human and veterinary medical arts. In addition, the compounds may also be used as injectible anthelmintic preparations. For this purpose, the active ingredient is admixed with suitable sterile carriers such as sterile water and isotonic saline solution.

Suitable clinical formulations containing the compounds of this invention can be administered orally in the form of tablets, capsules, elixirs and the like. The active compound is compounded with inert carriers such as, for example, gums, starches and sugars or it may be incorporated into gelatine capsules or formulated into elixirs which have the advantage of being susceptible to manipulations in flavor by the addition of standard, natural or synthetic flavoring agents.

Particularly useful anthelmintic formulations comprising the compounds of this invention for treatment of helminthiasis are either liquid suspensions ready to use or wettable or water-dispersible powders which are mixed with water prior to use.

A liquid-suspension formulation may contain from 50 to 55% w./v. (grams/liters) of the active compound together with a dispersing agent and stabilizing agent. A typical formulation is as follows:

| | |
|---|---|
| N—carbomethoxy-N'—[beta-diethylaminoethyl]-N''—[2-nitro-5-propylthiophenyl]guanidine | 50 to 55 parts by weight |
| Dispersing agent | ½ to 2 parts by weight |
| Stabilizing agent | 1 to 3 parts by weight |
| Preservative | as required |
| Water | Sufficient to make 100 volumes. |

Suitable dispersing agents are those containing sulphonate groups, for example sodium lignin sulphonate, or the sulphonated phenol or naphthol formaldehyde polymers. Bentonite may be employed as the stabilizing agent, although it is possible to use such protective colloids as carboxymethyl cellulose, sodium alginate and the like. The formulations can be prepared by mixing the active compound and water containing dissolved dispersing agents very vigorously by means of suitable mechanical mixing equipment.

A wettable or water-dispersible powder formulation may contain about 90 to 95% w./w. of the active compound together with a wetting agent and dispersing agent. A diluent such as kaolin can also be added if a concentration below about 98% w./w. is required. An anti-foaming agent and, in some cases, a stabilizing agent may be present. A typical formulation is as follows:

| | |
|---|---|
| N—carbomethoxy-N'—[beta-diethylaminoethyl]-N''—[2-nitro-5-propylthiophenyl]guanidine | 90 to 95 parts by weight |
| Wetting agent | ½ to 4 parts by weight |
| Stabilizing agent | 0 to 2 parts by weight |
| Anti-foaming agent | 0.01 to 1 part by weight |
| Water | 0 to 5 parts by weight |

Suitable wetting agents are the non-ionic alkylphenolethylene oxide adducts, such as an octylphenol or nonylphenol condensed with ten moles of ethylene oxide, or anionic materials, such as the synthetic aryl alkyl sulphonates, or sodium dibutyl napthalene sulphonate. In general, about 1% w./w. wetting agent is required. The anti-foaming agent employed may be either a silicone or such materials as ethyl hexanol, octanol and the like; and the stabilizing agent may again be chosen from bentonite or the water-soluble gums. Wettable or water-dispersible powder formulations are prepared by careful and adequate mixing of the active compound with other ingredients with or without the addition of some water using typical powder blending equipment such as a ribbon blender. The powder is stirred into water by the user before application in the field.

The following examples show particularly useful formulations:

| A. Tablet formulation | Grams per 1000 tablets |
| --- | --- |
| N—carbomethoxy-N'—[beta-diethylaminoethyl]-N"—[2-nitro-5-propylthiophenyl]guanidine | 200.0 |
| Lactose | 90.0 |
| Dicalcium phosphate, hydrous | 122.5 |
| Polyvinylpyrolidone | 25.0 |
| Polyethyleneglycol 1500 | 7.5 |
| Corn Starch | 50.0 |
| Magnesium Stearate | 5.0 |
| | 500.0 |

Mix the active compound, the lactose and the diacalcium phosphate. Dissolve the polyethyleneglycol 1500 and the polyvinylpyrrolidone in approximately 20 ml of water. Granulate the powder blend with the water solution, adding additional water if necessary, to product a damp mass. Pass the wet granulation through a 12 mesh screen; spread on trays and air dry at 35° C. Blend the dry granulates with the starch and the magnesium stearate. Compress into 500 mg tablets.

| B. Capsule formulation | Grams per 1000 capsules |
| --- | --- |
| N—carbomethoxy-N'—[beta-diethylaminoethyl]-N"—[2-nitro-5-propylthiophenyl]guanidine | 200.0 |
| Lactose | 198.0 |
| Magnesium Stearate | 2.0 |
| | 400.0 |

Blend the ingredients and fill into hard gelatine capsules.

| C. Elixir formulation | per 1000 ml |
| --- | --- |
| N—carbomethoxy-N'—[beta-diethylaminoethyl]-N"—[2-nitro-5-propylthiophenyl]guanidine | 40.0 g |
| Sodium citrate | 10.0 g |
| Sugar | 500.0 g |
| Glycerin | 200.0 g |
| Compound orange spirit | 10.0 ml |
| Alcohol | 100.0 ml |
| Amaranth | 0.1 ml |
| Water to total | 1000.0 ml |

Combine the above ingredients using standard techniques.

| D. Injectible formulation | mg/ml |
| --- | --- |
| N—carbomethoxy-N'—[beta-diethylaminoethyl]-N"—[2-nitro-5-propylthiophenyl]guanidine | 50.0 |
| Polyethylene Glycol 400 | 500.0 |
| Dimethyl Acetamide | 300.0 |
| Benzyl Alcohol | 20.0 |
| Water for Injection to q.s. | 1.0 ml |

Combine the above ingredients using standard techniques.

| E. Injectible formulation | mg/ml |
| --- | --- |
| N—carbomethoxy-N'—[beta-diethylaminoethyl]-N"—[2-nitro-5-propylthiophenyl]guanidine | 100.0 |
| Dimethyl Acetamide | 300.0 |
| Benzyl Alcohol | 20.0 |
| Polyethylene Glycol 400 to q.s. | 1.0 ml |

Combine the above ingredients using standard techniques.

Similarly, prepare formulations using other compounds of the present invention, e.g. N-carbomethoxy-N'-[beta-(N'-cyano-N"-methylguanidoethyl]-N"-[2-nitro-5-propylthiophenyl]guanidine.

I claim:

1. A compound of the formula

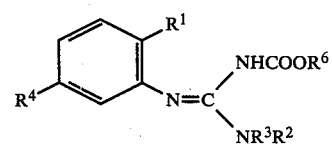

wherein $R^1$ is hydrogen, halo, nitro, $NHCOR^8$, or $NHSO_2R^8$;

$R^2$ and $R^3$ are independently selected from hydrogen, N-alkyl piperidyl, wherein the alkyl group has 1 to 4 carbon atoms, tetrahydropyranyl, morpholinyl, piperidyl, $C_1$ to $C_6$ alkyl substituted with hydroxy, $-SCH_3$, $COOR^{10}$, piperazinyl, pyridyl, $COR^9$, amino, and substituted amino, wherein the substituents on the substituted amino are selected from $C_1$ to $C_6$ alkyl,

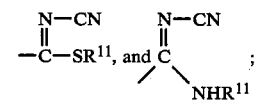

$R^4$ is $C_1$ to $C_6$ alkoxy;

$R^6$ is $C_1$ to $C_6$ alkyl and $C_1$ to $C_6$ alkyl substituted with $C_1$ to $C_6$ alkoxy, hydroxy, or amino;

$R^8$ is $C_1$ to $C_6$ alkyl, $C_1$ to $C_6$ alkyl substituted with phenyl or with halo, phenyl, or phenyl substituted with $C_1$ to $C_6$ alkyl or with halo;

$R^9$ is $C_1$ to $C_6$ alkyl, $C_1$ to $C_6$ acyl, or a peptide residue having up to three amino acids;

$R^{10}$ is hydrogen or $C_1$ to $C_6$ alkyl;

$R^{11}$ is $C_1$ to $C_6$ alkyl;

and the pharmaceutically acceptable acid addition salts thereof.

2. A compound according to claim 1 wherein $R^1$ is nitro, $R^3$ is hydrogen, $R^2$ is $C_1$ to $C_6$ alkyl substituted with $COOR^{10}$, pyridyl, amino or substituted amino wherein the substituents on the substituted amino are selected from $C_1$ to $C_6$ alkyl and

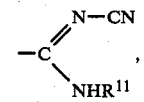

$R^4$ is $C_1$ to $C_6$ alkoxy, $R^6$ is $C_1$ to $C_6$ alkyl, and $R^{10}$ and $R^{11}$ are $C_1$ to $C_6$ alkyl.

3. N-methoxycarbonyl-N'-[beta-(N'-cyano-N"-methylguanidinoethyl)]-N"-[2-nitro-5-propyloxyphenyl]-guanidine, according to claim 2.

4. N-methoxycarbonyl-N'-[beta-(N'-cyano-N"-methylguanidinoethyl)]-N"-[2-nitro-4-propylthiophenyl]-guanidine, according to claim 1.

5. N-methoxycarbonyl-N'-[beta-(N'-cyano-N"-methylguanidinoethyl)]-N"-[2-nitro-5-propylthiophenyl]guanidine, according to claim 1.

6. A method of treating helminth infestation in mammals which comprises administering to an infected mammal an effective amount of a compound as claimed in any one of claims 3, 1, or 2.

7. An anthelminthic composition comprising an effective amount of a compound as claimed in any one of claims 3, 1, or 2 and a pharmaceutically acceptable carrier.

8. An anthelminthic composition, in injectible form, comprising an effective amount of a compound as claimed in any one claims 3, 1, or 2 and a pharmaceutically acceptable carrier.

9. An animal feed or drink comprising an effective amount of a compound as claimed in any one of claims 3, 1, or 2.

* * * * *

UNITED STATES PATENT AND TRADEMARK OFFICE
CERTIFICATE OF CORRECTION

PATENT NO. : 4,348,406
DATED : September 7, 1982
INVENTOR(S) : M. Mehdi Nafissi-Varchei It is certified that error appears in the above—identified patent and that said Letters Patent is hereby corrected as shown below:

In column 6, lines 63 to 68, delete claims 4 and 5:

"4. N-methoxycarbonyl-N'-/beta-(N'-cyano-N"-methyl-guanidinoethyl/-N"-/2-nitro-4-propylthiophenyl/-guanidine, according to claim 1.

5. N-methoxycarbonyl-N'-/beta-(N'-cyano-N"-methylguanidino-ethyl/-N"-/2-nitro-5-propylthiophenyl/guanidine, according to claim 1."

Renumber the remaining claims as follows:
in column 7, line 1, delete "6." and insert --4.--;
in column 7, line 5, delete "7." and insert --5.--;
in column 7, line 9, delete "8." and insert --6.--;
and in column 8, line 5, delete "9." and insert --7.--.

Signed and Sealed this

Thirtieth Day of November 1982

[SEAL]

Attest:

GERALD J. MOSSINGHOFF

Attesting Officer    Commissioner of Patents and Trademarks